United States Patent [19]

Kampen

[11] Patent Number: 5,177,008
[45] Date of Patent: Jan. 5, 1993

[54] PROCESS FOR MANUFACTURING ETHANOL AND FOR RECOVERING GLYCEROL, SUCCINIC ACID, LACTIC ACID, BETAINE, POTASSIUM SULFATE, AND FREE FLOWING DISTILLER'S DRY GRAIN AND SOLUBLES OR A SOLID FERTILIZER THEREFROM

[76] Inventor: Willem H. Kampen, 447 Blue Rock Dr., Charlotte, N.C. 28213

[21] Appl. No.: 537,779

[22] Filed: Jun. 18, 1990

Related U.S. Application Data

[63] Continuation-in-part of Ser. No. 381,179, Jul. 18, 1989, which is a continuation-in-part of Ser. No. 136,415, Dec. 22, 1987, abandoned.

[51] Int. Cl.⁵ .............................................. G12P 7/20
[52] U.S. Cl. ................................. 435/139; 435/145; 435/146; 435/159; 435/161
[58] Field of Search ............... 435/139, 141, 145, 146, 435/159, 161, 163

[56] References Cited

U.S. PATENT DOCUMENTS

| | | | |
|---|---|---|---|
| 2,169,245 | 8/1939 | Hildebrandt et al. | 195/38 |
| 2,772,207 | 11/1956 | Frankel et al. | 195/38 |
| 4,336,335 | 6/1982 | Muller et al. | 435/313 |
| 4,359,430 | 11/1982 | Heikkila et al. | 260/501.13 |
| 4,689,048 | 8/1987 | Fortsch et al. | 210/650 |
| 5,019,263 | 5/1991 | Haag et al. | 210/500.25 |

FOREIGN PATENT DOCUMENTS

| | | | |
|---|---|---|---|
| 51-039625 | 5/1976 | Japan | 101/00 |
| 55-045067 | 11/1980 | Japan | 101/12 |

OTHER PUBLICATIONS

Chico et al., "L. Alanine as an end product of glycolyisis in saccharomyces—cerevisiae growing under different hypoxic conditiones," CA79:177022 Bioss. 1978.

"Recovery of Chemicals Such as Glycerol, Dextrose, and Amino Acids from Dilute Broths", Brian D. Burris, pp. 1-39.

*Primary Examiner*—Robert J. Warden
*Assistant Examiner*—Timothy M. McMahon
*Attorney, Agent, or Firm*—Rhodes, Coats & Bennett

[57] ABSTRACT

This invention relates to the manufacture of ethanol and the recovery of economically significant amounts of such by-products therefrom as glycerol, betaine, L-pyroglutamic acid, succinic and lactic acid, potassium sulfate and a free flowing distiller's dry grain and solubles useful as an animal feed or a component of food for humans or as a premix for agricultural fertilizer and/or a feed additive. An important aspect of the recovery step is the utilization of a crossflow microfiltration system which includes inorganic membranes for the classification of the stillage.

37 Claims, 2 Drawing Sheets

PROCESS FOR MANUFACTURING ETHANOL AND FOR RECOVERING GLYCEROL, SUCCINIC ACID, LACTIC ACID, BETAINE, POTASSIUM SULFATE, AND FREE FLOWING DISTILLER'S DRY GRAIN AND SOLUBLES OR A SOLID FERTILIZER THEREFROM

RELATED APPLICATIONS

This application is a continuation-in-part of copending application Ser. No. 381,179 filed Jul. 18, 1989, which is, in turn, a continuation-in-part of copending application Ser. No. 136,415 filed 22 Dec. 1987, now abandoned the priority of which is claimed.

FIELD AND BACKGROUND OF THE INVENTION

This invention relates to the manufacture of glycerol, betaine, succinic and/or lactic acid, potassium sulfate, and L-pyroglutamic acid. More particularly the invention relates to the recovery of the above products as a result of the fermentation and distillation of raw materials into ethanol and stillage, from which a free flowing distiller's dry grain or solid fertilizer is produced.

The manufacture of each of the products named above by other processes has been known heretofore, and all have commercial uses. Ethanol is used as a beverage, a chemical, and a fuel derived from renewable resources, and is typically manufactured by fermentation and distillation processes starting from biological materials such as corn, wheat or other grain, sugar cane or beets, grapes or other fruit, potatoes, cassava, sweet sorghum, cheese whey or the like. Glycerol, while known to be produced in small quantities as a by-product of ethanol fermentation and distillation processes or yeast and yeast extract production, has been manufactured commercially only by processes which have soap as the primary product or which synthesize glycerol from petrochemical feed-stocks. Betaine is conventionally produced synthetically or by crystallization of the aqueous liquors of beet molasses. Succinic acid is conventionally synthesized from maleic or acetic acid or produced by means of a highly specific fermentation. Lactic acid is conventionally produced by fermentation with Lactobacillus delbrueckii, B. dextrolacticus, or similar microorganisms. Potassium sulfate is conventionally obtained by reacting sulfuric acid with potassium chloride. Potassium chloride usually occurs in nature as the mineral sylvine or sylvite.

Distiller's dry grain, characterized as with (DDGS) or without (DDG) solubles, is conventionally produced as a by-product of fermentation and distillation processes. As such the resulting DDG or DDGS is usually infused with sticky by-products such as glycerol so as to exhibit poor flowing qualities and be difficult to handle. If the substrate from which distillates are produced is a sugar cane or beet material, then the residue is typically used only as a liquid fertilizer, feed additive or treated as a waste.

The manufacture of ethanol is sufficiently well known and the interested reader is referred to the available literature for descriptions of the basic processes. The manufacture of glycerol is, by way of example, discussed in Hildebrandt U.S. Pat. No. 2,169,245;; Wallerstein U.S. Pat. No. 2,772,207, to which the interested reader is referred.

Some suggestion that glycerol might be recovered from stillage appears in a presentation by Burris entitled "Recovery of Chemicals Such as Glycerol, Dextrose, and Amino Acids from Dilute Broths" which was presented to the "International Conference on Fuel Alcohols and Chemical from Biomass" on Nov. 10-12, 1986 in Miami Beach, Fla. The process there disclosed includes a very precise sequence of operations including ultrafiltration (organic membranes with pore size of <0.1 microns), pH adjustment, filtration, ion exclusion, ion exchange, and carbon treatment. This sequence of operations has not proven to provide a commercially feasible glycerol recovery process.

Betaine production is, by way of example, discussed in U.S. Pat. No. 4,359,430 to Heikkila et al; Japanese Patent No. 51/039625; and Japanese Patent No. 80/045067. While the production of betaine from sugar beet molasses is a known commercially feasible process as described in the above listed patents, it is not known to produce betaine from stillage. This is because of a serious fouling of the chromatographic resin by yeast cells, microorganisms and other compounds. The manufacture of glycerol, betaine, succinic acid and free flowing distiller's dry grain, or the production of both betaine and glycerol from beet molasses stillage, by processes such as those to be described hereinafter has not, insofar as is known to the present inventor, been described in any prior patent or publication other than that which has resulted from the aforementioned priority application.

For the first time, it is now possible to recover betaine and/or glycerine from stillage of ethanol fermentations with sugar beet derivatives. The preparation of the feed with microfiltration and the two chromatographic separation steps for the production of pure glycerine and betaine are critical. Cross-flow microfiltration with inorganic membranes followed by enzymatic hydrolysis of proteinaceous matter and/or removal of potassium sulfate crystals in the permeate (if required) will yield a truly clarified stillage. The clarified stillage may now be concentrated to a very high solids concentration for further processing in two chromatographic separation steps, each with its own specific resin, yielding high purity glycerine and betaine streams. This novel process has several advantages over existing and different methods in use as described in the patents listed above, such as energy and water savings, reduced capitol investment, very high solids concentrations, high quality glycerine and betaine.

The processes and apparatus of the present invention contemplate the production of each or all or any combination of the products mentioned in a commercially feasible manner in a fermentation and distillation or similar process.

BRIEF DESCRIPTION OF THE INVENTION

More particularly, it is an object of this invention to produce glycerol as a valuable co-product of a fermentation process such as one which produces ethanol. In realizing this object of the present invention, the efficiency of the known ethanol producing fermentation and distillation processes is essentially maintained, while an additional valuable product is derived. More particularly, ethanol production follows known and widely published pathways of biochemical reactions. The present invention contemplates imposing pressures on such pathways in ways which result in enhanced generation of glycerol and/or other by-products, and permits such enhancement to be achieved with relatively little if any reduction of efficiency in the production of ethanol.

Likewise, a further object of this invention is the manufacture of betaine or betaine-HCl and/or L-pyroglutamic acid as a co-product of a fermentation from a substrate of sugar beets or similar materials.

Yet a further object of this invention is the recovery of lactic acid and other carboxylic acids from those fermentation processes, such as wet milled corn and certain wine fermentations, where lactic acid is produced in substantial quantities.

Another object of this invention is the production of distiller's dry grain with or without solubles or a solid fertilizer premix from a fermentation/distilation process that is so free of sticky by-products as to be essentially free flowing and thus easier to handle.

In its most general sense, fermented mash is distilled in a stripping column with the vaporized ethanol being removed from overhead. The remaining stillage is then clarified by centrifuging (if required) followed by microfiltration. The microfiltration step, in which particles in the range of 0.1 to 10 microns are separated from the stillage, is the key to the recovery of glycerol, betaine and by-products in such quantities as to be economically feasible. Earlier attempts (Burris) to recover glycerol had suggested ultrafiltration (separation of particle sizes of less than 0.1 microns) combined with other operative steps, however, due to fouling of ultrafiltration membranes, insufficient quantities of glycerol resulted to make the process economically feasible. The unexpected result of microfiltration with inorganic membranes is that, while the stillage is truly clarified, the subsequent recovery of by-products such as glycerol results in greatly enhanced quantities thereof, making its recovery for the first time commercially feasible.

Depending on the raw material, the separated clarified liquid is subjected to further processing by partial softening (if required), concentration, enzymatic hydrolysis of proteinaceous matter, removal of potassium sulfate crystals, one or more chromatographic separation steps (with different resins where more than one separation step is involved), concentration, and purification to produce glycerol, betaine, L-pyroglutamic acid, succinic acid, lactic acid, and/or potassium sulfate in economically acceptable quantities. Further, the resulting solids are freer of sticky by-products and thus more free flowing and easier to handle.

BRIEF DESCRIPTION OF THE DRAWING

Some of the objects of the invention having been stated, other objects will appear as the description proceeds, when taken in connection with the accompanying drawing, in which.

DETAILED DESCRIPTION OF THE INVENTION

While the present invention will be described more fully hereinafter with reference to the accompanying drawing, in which a preferred embodiment of the present invention is shown, it is to be understood at the outset of the description which follows that persons of skill may modify the invention here described while still achieving the favorable results of this invention. Accordingly, the description which follows is to be understood as being a broad, teaching disclosure directed to persons of skill in the appropriate arts, and not limiting upon the present invention.

Figure 1:
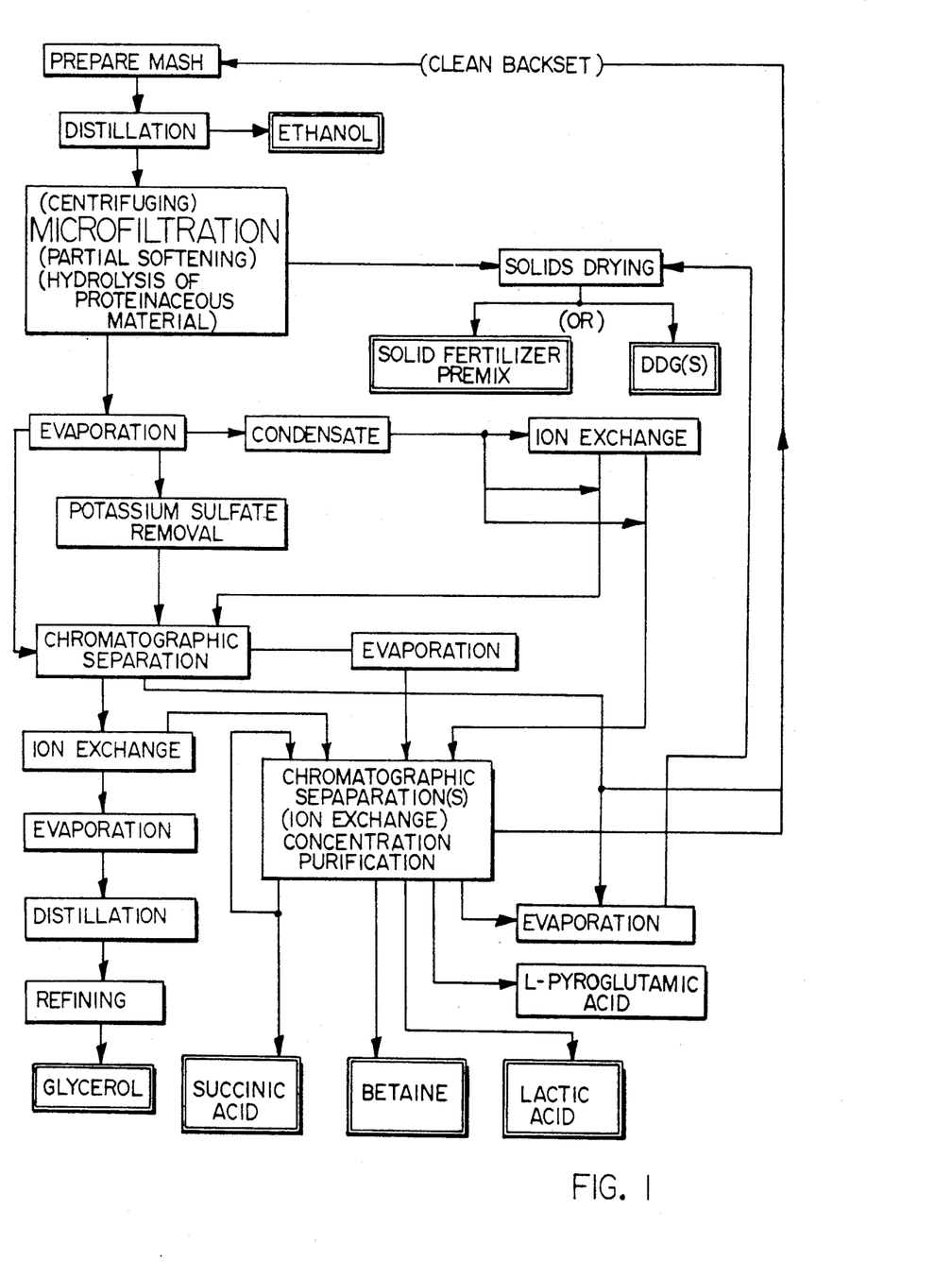
FIG. 1 is a schematic representation of the flow of the materials in the processes and apparatus of the present invention is shown.

Referring now more particularly to FIG. 1 accompanying this disclosure, there are depicted certain steps and apparatus which, in the sequence disclosed hereinafter, accomplish the objects of this invention. Certain steps and apparatus, being well known to those having skill in the relevant arts, have not been shown in detail but will be described for the reader.

It is known that the formation of ethanol in a fermentation process with yeast cells or other microorganisms is growth associated and that the formation of glycerol and succinic acid is interrelated. More specifically, in the Embden-Meyerhof pathway, NADH from triose phosphate oxidation exceeds the rate of acetaldehyde reduction, thus accounting for normal glycerol formation when the cell starved for ATP from glycolysis shifts excess NADH to the reduction of dihydroxyacetone phosphate to glycerol. Additional NADH is supplied through the Kreb's citric acid cycle. As used herein, NADH refers to nicotinamide adenine dinucleotide and ATP to adenosine triphosphate. In a conventional well run fermentation process without the recycle of stillage, some 48 grams of ethanol, 4.0 grams of glycerol, 0.6 gram of succinic acid, and small quantities of lactic acid are formed per 100 grams of reducing sugar consumed. Ethanol producers using a corn wet milling process generally have substantial quantities of lactic acid present in their fermented mash, as do certain wine and other fermentation.

Turning now to the drawing, regardless of the raw material, a fermented alcoholic mash is prepared with yeast cells and/or other microorganisms. Whether the enhancement of glycerol and/or succinic acid is the goal must first be determined in order to properly control the fermentation process. During cell growth, the formation of succinate is high, but during anaerobic fermentation succinate formation is low. Hence, variations in the cell growth fermentation process will permit some degree of control over the ratio of glycerol/succinic acid ultimately produced. Further, depending on the raw material and/or process conditions used for fermentation, betaine, L-pyroglutamic acid, lactic acid and other carboxylic acids may be recovered in sufficient quantities to be economically feasible.

Regardless of the raw material, after fermentation the next step is normally distillation, preferably in a stripping column, accompanied by overhead removal and collection of the ethanol vapors. The remaining still bottoms or stillage then contains all or any of the by-product components described hereinabove. The further processing will determine which of the by-products are recovered.

The first step after distillation, regardless of the by-products to be recovered, is the clarification process, which may begin with a centrifuging pretreatment with or without chemical treatment. In some cases, a protease(s), a protein digesting enzyme, is added in the pretreatment to break down peptides and proteins, which would tend to clog subsequent filtering membranes. Following pretreatment, if any, the stillage goes through the step of cross-flow microfiltration with inorganic membranes. Microfiltration, which is defined elsewhere in the disclosure as the subjection of the stillage to cross-flow microfiltration with a ceramic or inorganic membrane having pore sizes in the range of 0.1 to 10 microns separates the stillage into retentate and permeate, and is the critical step to producing a truly clarified stillage and the recovery of the by-products in economically feasible quantities.

The retentate, containing the larger solid particles, goes to fertilizer or animal feed processing. The permeate, depending upon the raw material used, may have to be softened to prevent fouling of the chromatographic separation resins used downstream. The permeate is then concentrated to as high a solids concentration as practicable (50-75%).

The concentrated permeate is then either directly passed on to chromatographic separation (preliminary to recovery of either glycerol, betaine, succinic acid, L-pyroglutamic acid or lactic acid) or is first subjected to a crystallization operation (for recovery of potassium sulfate from beet stillage). If the by-product is to be glycerol, the chromatographic separation used is ion exclusion and is followed by ion exchange, evaporation to a concentration of 80-85% glycerol, further distillation into almost pure glycerol, and refining into USP/CP or ultra-pure glycerol.

The by-product stream from the aforementioned chromatographic separation step goes to animal feed processing or to a second separation step, which may be chromatography (for betaine where the raw material is sugar beets) and/or physico-chemical separation for the production of succinic acid, lactic acid, L-pyroglutamic acid and/or betaine (where the raw material is sugar beets). Where corn is the raw material for a wet milling process, the economically feasible recovery of lactic acid is possible through the second chromatographic separation step. With sugar beets, betaine and L-pyroglutamic acid may be recovered as well. In such case, the first chromatographic separation yields glycerol and betaine. These are separated in the second chromatographic step and each product is purified, concentrated, and refined. Except for betaine, sugar cane produces the same products as sugar beets.

The first process parameter to be addressed for enhanced glycerol and/or succinic acid formation during fermentation relates to the form of yeast used in the fermentation process. It has been determined that a properly immobilized organism will enhance and increase production of glycerol and succinic acid. These results are achieved where the yeast is in a stable ionic and high density matrix, as illustrated in the following example.

EXAMPLE 1

A mash prepared of ground whole corn was subjected to jet cooking for two minutes at 149° C. and then to liquefaction at a pH of 6.3 to a dextrose equivalent (DE) of 20.3, and to saccharification to DE 36 at pH 4.5. Immobilized yeast cells were prepared by mixing a 1.5 weight percent sodium alginate solution with the preferred ratio of hydrated yeast cells and sterilized sand. The resulting slurry was poured through a 12 mesh screen into an aqueous solution of 0.5M $CaCl_2$ and 1.5 weight percent glucose at pH 4.6 and ambient temperature. On contact with the calcium chloride, the drops formed beads which, after 24 hours in a refrigerator at 4° Celsius, gelatinized into firm beads with diameters of 2-4 mm. The mash was then fermented in two batches at 34° Celsius with free and immobilized yeast cells at concentrations of 5.0 grams per liter. Fermentation was performed in a batch process with no recycling of stillage and adjustment of pH to 5.0 using NaOH. Comparing the two batches, yields were as follows:

|  | Grams/100 Grams of Reducing/Sugar(RS) | |
|---|---|---|
|  | Glycerol | Succinic Acid |
| Free Cells | 3.38 | 0.67 |
| Immobilized | 4.09 | 0.87 |

Other process parameters which are contemplated as being subject to adjustment in accordance with this invention include yeast cell concentration and DE or carbohydrate concentration. As yeast cell concentration and carbohydrate concentration rise, production of glycerol and succinic acid are enhanced. These characteristics are illustrated in the following example:

EXAMPLE 2

A mash was prepared from ground whole milo and fermentation started at pH 4.9 and DE 27 using free yeast cells and at a temperature of 33° Celsius. Fermentation was performed in batches, without stillage recycle. Yields, related to yeast cell and carbohydrate concentration, were as follows:

| Yeast cell concentration per $10^6$ ml | DE | grams/100 grams RS | |
|---|---|---|---|
|  |  | Glycerol | Succinic Acid |
| 100 | 27 | 3.03 | 0.49 |
| 300 | 27 | 3.07 | 0.52 |
| 500 | 27 | 3.19 | 0.61 |
| 500 | 46 | 3.37 | 0.64 |
| 1,500 | 90 | 5.01 | 0.88 |

These results reflect enhanced glycerol and succinic acid production following from increased concentration of yeast cells and carbohydrates during fermentation.

Still other process variables which are contemplated by this invention as being optimized for the production of the desired products while maintaining ethanol production include osmotic pressure during fermentation; concentration of dissolved carbon dioxide; pH; temperature; selection of the microorganism used; the mode of fermentation; and the formulation and preparation of fermentation media. More precisely, increased osmotic pressure from recycling stillage, increased solute concentration, and/or increased temperature increases production of glycerol and succinic acid, as does increased dissolved carbon dioxide. Yeast cells, as most microorganisms, are able to regulate its internal pH quite effectively within a range of mash pH of from about 3 to about 7, and thus the effect of process variations in pH may appear minimal. It has been determined, however, that production of glycerol and succinic acid is enhanced where an essentially constant pH is maintained during the first half of the fermentation step (when the bulk of glycerol and succinic acid are produced) by the addition of a suitable alkali such as sodium carbonate. The fermentation media, or mash, characteristics will affect the production of glycerol and succinic acid due to the interacting effects of the raw material itself, the concentration of any liquefying enzyme, the ratio of fermentable sugars to nonsugars, the type of nonsugars present, and the nutritional requirements of the particular fermentation microorganism chosen.

Proper selection of the parameters described above will result in enhanced production of glycerol and succinic acid as contemplated by this invention. The following examples include illustrations of variation in the various parameters and the effects on glycerol and succinic acid production of those variations.

EXAMPLE 3

A mash prepared from ground whole corn was subjected to jet cooking for 3 minutes at 152° Celsius, was liquefied to DE 20.6 and partially saccharified. Batches of the mash were then fermented and distilled using process parameters as set forth in the following table, with yields as noted.

| Process | Batch | | | |
| Parameter | A | B | C | D |
| --- | --- | --- | --- | --- |
| YCC | 1.2 | 3.1 | 9.0 | 26.5 |
| DE | 33.2 | 56.3 | 78.7 | 78.7 |
| Recycle | 0 | 38.3 | 44.1 | 71.4 |
| Temperature | 30 | 34 | 35 | 35 |
| pH | 4.5 | 5.5 | 6.0 | 5.0 |
| Head | atm. | 1.7 | 2.3 | 1.2 |
| Yeast type | free | immob. | immob. | immob. |
| Time | 58 | 39 | 12 | 9 |
| Yields grams/100 grams RS | | | | |
| Ethanol | 44.9 | 44.1 | 42.0 | 44.7 |
| Glycerol | 4.8 | 5.8 | 8.3 | 12.3 |
| Succinic acid | 0.6 | 0.7 | 1.1 | 1.4 |

In the table, YCC refers to yeast cell concentration in grams per liter with approximately $10^{10}$ cells per gram. DE refers to dextrose equivalent after saccharification. Recycle refers to the percentage of recycled stillage in the mash being processed. Temperature is the temperature of fermentation in degrees Celcius. The reference to pH is to the value at which pH was maintained during the first half of the fermentation by the addition of sodium carbonate. The "Head" was head pressure in psig. Time is in hours for fermentation.

Considering the tabulated examples together, it is noted that production of glycerol and succinic acid was substantially enhanced with little adverse effect on ethanol production.

EXAMPLE 4

A mash was prepared from clarified and pasteurized blackstrap molasses, and batches of the mash were then fermented and distilled using process parameters as set forth in the following table, with yields as noted.

| Process | Batch | | | | |
| Parameter | A | B | C | D | E |
| --- | --- | --- | --- | --- | --- |
| YCC | 1.0 | 3.0 | 18.2 | 32.0 | 20 |
| RS | 184 | 184 | 192 | 200 | 200 |
| Recycle | 0 | 24.7 | 43.0 | 37.9 | 48.4 |
| Temperature | 30 | 34 | 34 | 35 | 35 |
| Head | atm. | 0.9 | 1.8 | 2.1 | 1.2 |
| Yeast type | free | free | immob. | immob. | immob. |
| Fermentation | batch | batch | batch | cont. | batch |
| Time | 51 | 27 | 10 | 6 | 12 |
| pH | 4.5 | 5.0 | 6.0 | 5.5 | 5.0 |
| Yields grams/100 grams RS | | | | | |
| Ethanol | 48.3 | 47.8 | 43.9 | 46.4 | 45.1 |
| Glycerol | 3.7 | 4.3 | 8.4 | 5.1 | 10.9 |
| Succinic acid | 0.5 | 0.6 | 1.0 | 0.8 | 1.2 |

In the table, RS refers to reducing sugar concentration in grams per liter and "Fermentation" refers to a choice between batch and continuous processes, while the other parameters are as identified above in the description of Example 3.

It will be observed that parameters may be found at which the production of glycerol and succinic acid drop below the maximized levels. However, the maximized levels of production of the by-products sought by the present invention is attained without significant impairment of ethanol production.

EXAMPLE 5

In order to illustrate other processes without characterizing the additional process as achieving optimal production of glycerol and succinic acid, a clarified wood hydrolyzate was prepared from yellow pine and processed by batch fermentation with pH held constant for 25 hours, without recycling of stillage and with parameters and yields as follows:

| Process | Batch | | |
| Parameter | A | B | C |
| --- | --- | --- | --- |
| YCC | 15.0 | 40.0 | 40.0 |
| RS | 54.3 | 54.3 | 74.1 |
| Temperature | 31 | 33 | 34 |
| Head | atm. | 0.3 | 1.2 |
| Yeast type | free | immob. | immob. |
| Fermentation | batch | batch | batch |
| Time | 68 | 43 | 41 |
| pH | 5.0 | 5.5 | 5.0 |
| Yields grams/100 grams RS | | | |
| Ethanol | 29.4 | 34.5 | 40.4 |
| Glycerol | 3.4 | 3.9 | 6.9 |
| Succinic acid | 0.5 | 0.8 | 1.1 |

In accordance with this invention, a fermented mash prepared in accordance with any of the above examples is then further processed to yield pure glycerol derived from natural sources (and thus of kosher purity) and/or succinic acid. As a result of the further processing, the end residue solids may be dried to yield DDG and DDGS and/or fertilizer premix which is free flowing and more readily handled than are the similar products of other prior processes, due to the removal of the glycerol.

Generally, the first further processing step is distillation of the fermentation to produce ethanol. Such distillation may be by use of a stripping column capable of handling a solids containing stream. The still bottoms or stillage is then centrifuged (if required) and the centrate processed further in a clarification step, removing the dispersed solids to obtain a (sparkling) clear liquid. Clarification is accomplished with (cross-flow) microfiltration systems containing ceramic or mineral membranes. In this process particles in the range of 0.1-10 microns, depending on the membrane selected are separated from the thin stillage. High and stable fluxes may be obtained through computer controlled backflushing and proper membrane selection. These new microfiltration membranes are known as such and are commercially available from known suppliers. Such known apparatus may be incorporated into the overall apparatus which practices the processes of this invention. A chemical clarification process may proceed by taking up to 20 percent of the stillage and liming it to a pH of 9.0 to 12.0 while at or near boiling. The remainder of the stillage is adjusted to a pH range of 4.5 to 7.5 with sodium hydroxide, calcium hydroxide and/or sodium carbonate at temperatures as high as practicable. The two portions are then mixed and a precipitate of salt forms, the separation of which is improved by the addition of polyelectrolytes, followed by centrifugation. Depending upon the raw material following microfiltration or chemical clarification is a (partial) softening step; mainly for the reduction of the divalent cation levels of calcium and magnesium. This will prevent the plugging and fouling of the downstream ion exclusion resin by salt deposits of divalent cations due to potential process upsets which would considerably reduce the operating efficiency. As the stillage is clarified, it may be passed to and through an evaporator to remove as much water as possible and effect as high a solids concentration as is practicable. Due to proper clarification, the overall heat transfer coefficient involved will be considerably improved over thin stillage which has not been clarified, while the fouling of heat transfer surfaces will also be minimized.

The clarified and concentrated stillage is passed to an ion exclusion apparatus such as that available from Illinois Water Treatment Company of Rockford, Ill. and which contains a suitable resin material such as IWT's SM-51-Na resin or other similar resin available from Dow Chemical as Dowex 50-WX8. As the material passes through the ion exchange apparatus, glycerol is "retained" while other ionic constituents are passed into an effluent stream. Recovery efficiencies are in the range of from about 80% to about 98%, and the purity of the glycerol recovered is in a range of from about 80% to about 90%. The apparatus may be a simple or multiple column system used as a pulsed bed or a simulated moving bed. Recycling may be used to maintain or increase product purity and/or recovery efficiency. Condensate as is from any evaporators used in the apparatus may serve as desorbent, with desorbent to feed ratios in the range of from about 1.6 to about 3.0. Such a column is in ionic equilibrium and requires no regeneration. Effluent from a glycerol recovery ion exclusion apparatus, after concentration, may be passed through a comparable apparatus for recovery of succinic acid. The dilute succinic acid product is concentrated in an evaporator and purified through crystallization. The resulting by-product stream of the ion exclusion step, before or after succinic acid recovery, is ideal for use as a backset in the fermentation. It is a "clean" stream, which will increase osmotic pressure levels as well as reduce process water requirements.

The glycerol stream recovered from the ion exclusion apparatus and process may be further purified in a mixed bed ion exchanger and then concentrated and purified to any desired grade. Such concentration and purification may, for example, be accomplished by the use of an energy efficient vacuum/steam multiple effect evaporator, and distillation and refining unit such as those available from G. Mazzoni SpA of Italy, with the more concentrated glycerol being deodorized, bleached, filtered and/or polished as desired.

As a further example, the production of glycerol and succinic acid without specific preparation of a stillage having enhanced levels of those constituents is believed valuable.

EXAMPLE 6

Stillage from a facility for the production of ethanol from wet milled corn was centrifuged and the thin stillage subjected to microfiltration in a ceramic membrane unit. The clear permeate was partially softened and then concentrated through evaporation to 73 weight percent solids, while it still behaved like a Newtonian fluid. It was fed at about 60 percent solids to an IWT Adsep system consisting of a single three inch I.D. column with a bed height of 62.25 inches of IWT SM-51-Na resin. The concentrate was fed at a rate of 2 GPM/square foot, with 20% feed pulse at 1.442 liters/pulse. The glycerol containing effluent was passed through an IWT mixed bed ion exchange unit to improve purity; then adjusted to pH 7.0 using NaOH; then, using Mazzoni equipment, concentrated by evaporation to 83.1 weight percent glycerol; and distilled and refined to a CP/USP grade glycerol of high quality. Constituents in the material at stages in the process were as summarized in the following table showing weight distributions.

| Constituent | Stillage | Clarified Conc. Stillage | Adsep Effluent | Final Product |
|---|---|---|---|---|
| Total solids | 7.37 | 5.01 | 1.21 | Trace |
| Protein | 2.36 | 1.07 | Trace | — |
| Carbohydrates | 1.19 | 0.38 | 0.03 | — |
| Fat | 0.007 | 0.003 | 0.001 | — |
| Ash | 0.84 | 0.77 | 0.09 | — |
| Lactic acid | 1.42 | 1.32 | 0.05 | Trace |
| Succinic acid | 0.09 | 0.08 | 0.006 | — |
| Other | 0.343 | 0.306 | 0.026 | Trace |
| Glycerol | 1.01 | 0.96 | 0.94 | 0.924 |
| Water | 92.63 | 8.91 | 15.687 | 0.007 |
| Total | 100.00 | 13.92 | 18.04 | 0.931 |
| Percent Glycerol | 1.01 | 6.90 | 5.19 | 99.25 |
| Na, ppm | 10,700 | | 740 | |
| K, ppm | 4,500 | | 70 | |
| Mg, ppm | 960 | | 70 | |
| Ca, ppm | 240 | | 4 | |
| Mn, ppm | 90 | | 2 | |

A further example of the recovery of ethanol, glycerol, succinic acid and lactic acid follows:

EXAMPLE 7

A mash prepared of ground degerminated yellow dent number two corn was cooked and liquefied to a dextrose equivalent (DE) of 21.3. The mash was then partially saccharified and subsequently fermented with co-immobilized gluco-amylase and Saccharomyces cerevisiae yeast with the following process parameters and yields:

| Process Parameter | Batch A | B | C |
|---|---|---|---|
| YCC | 107 | 118 | 15 |
| DE at start of ferm. | 82 | 84 | 21 |
| Recycle | 83 | 84 | 40 |
| Temperature | 38 | 39 | 34 |
| pH | 6.8 | 7.2 | 5.0–3.9 |
| Head | 15.6 | 16.0 | atmos. |
| Time | 7.4 | 7.9 | 49 |
| Yields grams/100 grams RS | | | |
| Ethanol | 43.9 | 43.1 | 47.9 |
| Glycerol | 17.0 | 20.2 | 9.1 |
| Succinic acid | 1.8 | 1.9 | 0.8 |
| Lactic acid | trace | trace | 11.9 |

The reference to pH is to the value at which pH is maintained during the first two thirds of the fermentation by the addition of sodium carbonate in the process of column A and sodium hydroxide/sodium sulfite in the process of column B. The "Head" was fermenter head pressure in psig. Time is in hours for fermentation.

The process of column C differs from those of columns A and B. The process of column C was based on the production of ethanol from wet milled corn; fermentation was continuous, and pH was permitted to vary over time from a starting pH of 5.0 to an ending pH of 3.9.

Considering the tabulated examples together, it is noted that production of glycerol was substantially enhanced with relatively little adverse affect on ethanol production. It is possible to further enhance glycerol and succinic acid production, although ethanol production falls substantially as such further enhancement is achieved.

In the processes of this Example 7, the fermented mash is distilled to strip off ethanol. The bottoms or whole stillage is clarified to obtain a clear liquid. In the preferred process, as previously described, cross flow microfiltration systems with inorganic membranes having pore sizes in the range of from about 0.1 microns to about 10 microns are used to remove particulate matter. Such inorganic membranes for the first time allow proper stillage clarification. Hot stillage, either as received or after centrifugation and/or filtration to remove coarse particles, may now be processed. Preferably, computer controlled backflushing (at high pressure if necessary) will allow for high on-line stream factors for the microfiltration modules and will in most cases eliminate the need for (harsher) chemical cleaning. The feed may be pretreated chemically to produce a floc, which under controlled conditions, will form a "dynamic membrane" layer and improve the clarification. Known filtration apparatus having the characteristics recited may be incorporated in the overall apparatus which is used in practicing this invention.

Microfiltration yields a concentrate or retentate which is further processed into DDG or DDGS, a feed product for animals or a component for human food products, or a fertilizer base to which may be added the by-product stream from chromatographic separation processes described hereinafter. The microfiltration permeate may, if necessary, be softened to remove divalent cations which could otherwise foul the downstream chromatographic separation resin(s).

The clarified stillage is next concentrated to as high a solids concentration as practicable. Due to the clarification, the overall heat transfer coefficients involved have been improved while scaling of heat exchange surfaces has been minimized. Where the fermentation substrate is a sugar beet product, cooling and/or addition of sulfuric acid will bring about the formation of potassium sulfate, which may be recovered through crystallization to yield yet another valuable by-product.

Chromatographic separation of the clarified, concentrated stillage then follows. In a preferred method and generally as disclosed in the priority application identified above, the material passes through an ion exclusion apparatus containing a suitable resin. Glycerol, as a non-ionized compound, is unaffected by the Donnan potentials and distributes itself freely inside the aqueous pore structure of the resin beads, while the ionic compounds pass around the beads and exit the apparatus first. Ion exclusion and exchange resins may be kept in the potassium monovalent form, which will maximize the separation between ionic and nonionic components as well as improve formation of potassium sulfate. Attainable glycerol recovery efficiencies are in the range of from about 80% to about 98%, and the purity of the recovered glycerol is in the range of from about 80% to about 98% as well.

The chromatographic separation apparatus may be a single or multiple column system used as a pulsed bed or a simulated moving bed in a continuous process. The condensate from any evaporators used in the process may be used as the desorbent, thus minimizing make up water requirements. Desorbent to recovered glycerol ratios are in the range of from about 10 to about 25. Such a system is in ionic equilibrium and does not normally require regeneration. The by-product stream, containing succinic and lactic acids, may be concentrated to as high a solids content as practicable and the succinic and lactic acids separated in a further chromatographic separator using either acid retardation or ion exclusion. The succinic acid stream is concentrated and the acid is recovered through crystallization. Similarly, lactic acid may be recovered at this point by standard processes. Ion exchange of the product streams will in most cases improve product purity. Depending upon the resin, starting substrate and operating conditions used, betaine and glycerol may exit the chromatographic separation together. It is then necessary to use the following (smaller) chromatographic separation to produce a pure betaine stream from which betaine may be recovered with standard processes. Using a resin such as IWT-AM-63, excellent separations were obtained. Over 98 percent of the glycerol and over 92 percent of the betaine were recovered making it simple to produce pure products. The desorbent may be condensate produced in the overall process. In a large scale test at 60° C., the desorbant used was 5.7 pounds of water per pound of betaine and 13.6 pounds of water per pound of glycerol, while 0.81 pounds of betaine per minute and per square foot and 0.34 pounds of glycerol per minute and per square foot were obtained.

The glycerol product stream is concentrated in double effect LTV evaporators to approximately 85% dry solids. Feed forward systems employing a thermocompressor with high pressure steam and feed backward systems using greater quantities of lower pressure steam may be used. The concentrated crude glycerin may be neutralized before it is fed into the rectifying section of a high efficiency distillation column. Through evacuation and direct steam injection the column partial pressure is kept low to minimize glycerol decomposition. Glycerol leaves the evaporators for condensors, and then is deodorized with steam and bleached with granular activated charcoal. Consumption of charcoal is minimized due to the already relatively purified state of the glycerol feedstock. The product then passes through polishing filters and a cooler to produce ultra pure glycerin. The evaporation, distillation and refining equipment are known, as such, and is available with the inclusion of design improvements over conventional glycerin apparatus from G. Mazzoni SpA of Italy.

It is also contemplated for this invention that glycerol, succinic acid, betaine, L-pyroglutamic acid, potassium sulfate and a solid fertilizer may be produced from beet molasses stillage without the specific preparation of a stillage having enhanced levels of glycerol and succinic acid. Such a process is illustrated by the following:

EXAMPLE 8

Figure 2:
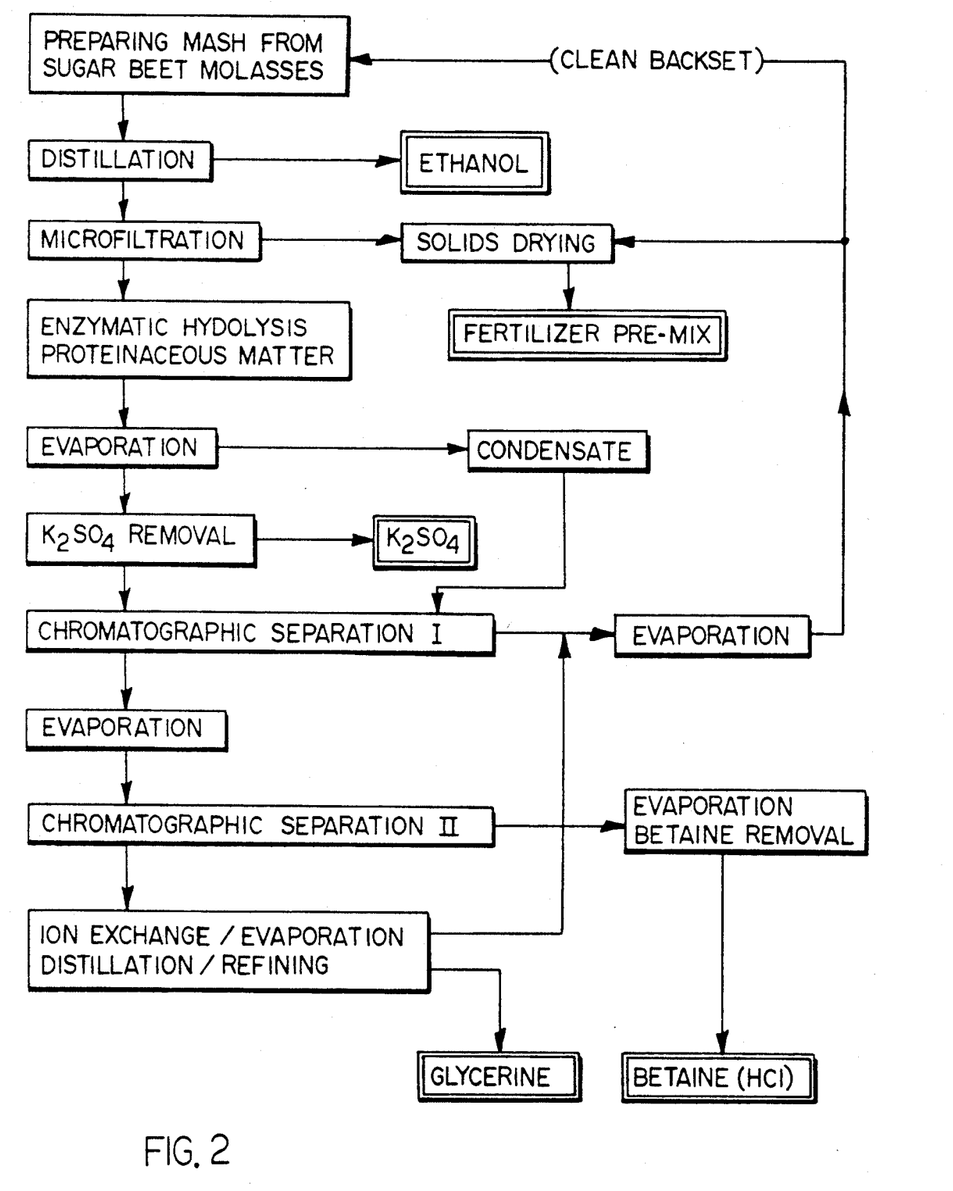
FIG. 2 is a schematic representation similar to FIG. 1 except illustrating the flow of materials in a system recovering glycerol and betaine.

As described in FIG. 2, stillage from a plant producing ethanol from sugar beet molasses, was processed into ultra-pure glycerine and betaine-HCl in a continuous process. Enhanced formation of glycerol was not pursued during the fermentation. The hot stillage was clarified in a cross-flow microfiltration unit with 0.2 micron alpha aluminum oxide membranes. The permeate obtained was treated enzymatically at 50° C. to hydrolize proteinaceous matter and consequently evaporated to a solids concentration of over 66 wt. %. Through cooling and crystallization in a malaxeur, potassium sulfate crystals were formed which through centrifugation, washing and drying were recovered as a technical-grade $K_2SO_4$, which is more valuable then leaving it in the remaining stillage (fertilizer). The centrate was then fed to the first chromatographic separation system in which a mixture of betaine plus glycerol is separated from the rest. This ion exclusion system used a strong acid cation exchange resin in the potassium form with a mean particle size of approximately 375 micron and a moisture retention capacity of approximately 52.5% (H+ form; IWT SM-51). The product stream contained 36.3% total solids with approximately 92% purity in terms of glycerine plus betaine. Water was used as the desorbent. This product stream was next concentrated to 75% total solids and fed to a second, considerably smaller chromatographic system, which contained a polystyrene strong base anion exchange gel resin in the sulfate-form. Its mean particle size is approximately 350 micron and its water holding capacity between 41-46%. Both resins used meet all requirements for use in food applications (FDA Regulation Title 21, Subpart A, Section 173.25). Water was again the desorbent. This second chromatographic separation step did yield a glycerine stream with a purity of 97.6% (after mixed-bed ion exchange) and a betaine stream with a purity of 88.2%. The glycerine stream was easily further processes into ultrapure glycerine with G. Mazzoni SpA equipment. The betaine stream was further processed into pure betaine and betaine HCl. Overall recovery was 88.5% for glycerine and 93.2% for betaine.

The remaining stillage was combined with the by-product stream from the first chromatographic separation step, the retentate from the microfiltration step as well as the by-product streams from glycerine purification and then concentrated and dried into a solid fertilizer premix or feed additive.

In the second chromatographic separation step, another resin used also resulted in the production of pure glycerine and betaine streams. This resin is a strong acid cation exchange resin in the calcium-form with a mean particle size of 350 micron and a moisture retention capacity (H+ form) of 57.5-61.0%. Succinic acid and L-pyroglutamic acid were not recovered.

The concentration of key components in weight percent at intermediate stages was as follows:

| | Total Solids | Suspended Solids | Glycerol | Betaine |
|---|---|---|---|---|
| Stillage | 7.5 | 1.0 | 0.7 | 1.5 |
| Microfiltration Permeate | 6.5 | | 0.7 | 1.5 |
| Evaporator Concentrate | 60.0 | | 6.3 | 13.5 |
| After First Chromatographic Separation | 36.3 | | 10.6 | 22.7 |
| Evaporator Concentrate | 75.0 | | 22.0 | 47.0 |
| Glycerol Stream | 38.2 | | 37.3 | |
| After Second Chromatographic Separation Betaine Stream | 23.7 | | 0.5 | 20.9 |
| After Second Chromatographic Separation | | | | |

In the drawing and specifications, there has been set forth a preferred embodiment of the invention and, although specific terms are used, the description thus given uses terminology in a generic and descriptive sense only and not for purpose of limitation.

What is claimed is:

1. A continuous process for recovering glycerol from stillage produced from the fermentation and distillation of such biological materials as corn, wheat, other grains, sugar cane, sugar beets, grapes, other fruit, potatoes, cassava, sweet sorghum, and the like which results in ethanol and said stillage, said continuous process comprising the steps of
    a) clarifying the stillage by subjecting the stillage to a cross-flow microfiltration process utilizing inorganic membranes having pore sizes in the range of 0.1 to 10 microns.
    b) passing the clarified stillage through an ion exclusion material for separating chromatographically glycerol from other constituents of the clarified stillage, and
    c) purifying the separated glycerol.

2. The process according to claim 1 wherein the step of clarifying further comprises initially centrifugally separating solids from liquid constituents prior to subjecting the stillage to microfiltration.

3. The process according to claim 1 wherein when sugar beets are used as the stillage producing material, the clarified stillage from step (a) is enzymatically treated to hydrolize proteinaceous material.

4. The process according to claim 1 wherein when sugar beets are used as the stillage producing materials, the clarified stillage is concentrated to 50-75% solids and the resulting potassium sulfate crystals are removed.

5. The process according to claim 1 wherein the permeate from the microfiltration step is concentrated to as high a solids concentration as practicable before passing through said ion exclusion material.

6. The process according to claim 1 wherein said purifying step comprises the steps of ion exchange, evaporation to a concentration of 80-85% glycerol, further distillation and refining into glycerol having a purity of at least 99.7%.

7. The process according to claim 1 wherein said stillage is produced by the steps of:
    a) preparing a mash from biological materials;
    b) fermenting said mash with sufficient yeast to produce a fermented mash having at least about 9 grams of glycerol and 40 grams of ethanol per 100 grams of reducing sugar in the mash;
    c) distilling the fermented mash to produce ethanol in said stillage.

8. The process according to claim 7 wherein said yeast comprises immobilized yeast cells.

9. The process according to claim 7 wherein said step of fermenting said mash comprises the step of mixing with said mash yeast cells in a concentration in excess of 100 grams per liter.

10. The process according to claim 7 wherein said mash is so prepared as to have a dextrose equivalent of at least about 80.

11. The process according to claim 7 wherein the pH of the mash is maintained substantially constant during the first two-thirds of said fermentation process.

12. The process according to claim 7 wherein the step of fermenting said mash comprises adding sufficient yeast to produce a fermented mash having at least about 15 grams of glycerol and 40 grams of ethanol per 100 grams of reducing sugar in the mash.

13. The process according to claim 7 wherein said steps of clarifying, chromatographic separation, and purifying are a continuous process.

14. A continuous process for recovering glycerol and betaine from stillage produced from the fermentation and distillation of sugar beets which results in ethanol and said stillage, said continuous process comprising the steps of:
a) clarifying said stillage by subjecting the stillage to a cross-flow microfiltration process utilizing inorganic membranes having pore sizes in the range of 0.1–10 microns;
b) subjecting the clarified stillage to a first chromatographic separation by passing the clarified stillage through an ion-exclusion apparatus for separating glycerol and betaine as a mixture from other constituents of the clarified stillage;
c) subjecting the glycerol/betaine mixture to a second chromatographic separation by passing the mixture through a second ion exclusion apparatus in which the glycerol is separated from the betaine; and
d) purifying the separated glycerol and betaine.

15. The process according to claim 14 wherein said step of clarifying further comprises initially centrifugally separating solids from liquid constituents prior to subjecting the stillage to microfiltration.

16. The process according to claim 14 wherein the clarified stillage from step (a) is enzymatically treated to hydrolize proteinaceous material.

17. The process according to claim 14 wherein the clarified stillage is concentrated to 50–75% solids and the resulting potassium sulfate crystals are removed.

18. The process according to claim 14 wherein the glycerol/betaine stream from the first chromatographic separation step is concentrated to approximately 75 wt. percent before passing onto the second chromatographic separation step.

19. The process according to claim 14 wherein the glycerol stream and the betaine stream which issue from the second chromatographic separation step are each subjected to ion exchange, further concentration, and purification by distillation and refining into glycerol and crystallization into betaine-HCl or betaine.

20. The process according to claim 14 wherein the permeate from the clarification step is subjected to a crystallization process resulting in potassium sulfate crystals and a permeate containing glycerol/betaine which is passed on to said first chromatographic separation step.

21. The process according to claim 14 wherein said first chromatographic separation separates essentially glycerol and betaine into a first stream and a second stream contains other products including at least one of such products as succinic acid, lactic acid and L-pyroglutamic acid, and said second stream is subjected to further chromatographic separation stages to separate each, all and any combination of the other products from the remaining products.

22. The process according to claim 14 wherein said fermentation, distillation, clarification, chromatographic separation, and purification are all a part of a continuous process.

23. A continuous process for recovering at least two of the group containing glycerol, betaine, succinic acid, lactic acid, L-pyroglutamic acid from stillage produced from the fermentation and distillation of such biological materials as corn, wheat, other grain, sugar cane, sugar beets, grapes, other fruit, potatoes, cassava, sweet sorghum, and the like which result in ethanol and said stillage, said continuous process comprising the steps of:
a) clarifying the stillage produced from the distillation of the fermented mash by subjecting the stillage to a cross-flow microfiltration process utilizing inorganic membranes having pore sizes in the range of 0.1–10 microns;
b) passing the clarified stillage through a succession of ion exclusion apparatuses for chromatographically and/or physico-chemically separating each product from the other constituents of the clarified stillage; and
c) purifying the separated product.

24. The process according to claim 23 wherein when sugar beets are used as the stillage producing material, the clarified stillage from step (a) is enzymatically treated to hydrolize proteinaceous material.

25. The process according to claim 23 wherein when sugar beets are used as the stillage producing material, the clarified stillage is concentrated to 50–75% solids and the resulting potassium sulfate crystals are removed.

26. Glycerol manufactured in accordance with the process of claim 1.

27. Glycerol and betaine manufactured in accordance with the process of claim 14.

28. Glycerol, betaine and potassium sulfate manufactured in accordance with the process of claim 14.

29. Glycerol betaine, and L-pyroglutamic acid manufactured in accordance with the process of claim 14.

30. Glycerol and one of the group consisting of betaine, succinic acid, lactic acid, and L-pyroglutamic acid manufactured in accordance with the process of claim 23.

31. A continuous process for the recovery of betaine from beet stillage produced from the fermentation and distillation of sugar beets which results in ethanol and said beet stillage, the continuous process comprising the steps of:
a) clarifying said stillage produced from the distillation of fermented sugar beet mash by subjecting the stillage to a cross-flow microfiltration process utilizing inorganic membranes having pore sizes in the range of 0.1–10 microns;
b) subjecting the clarified stillage to chromatographic separation by passing the clarified stillage through an ion exclusion apparatus for separating betaine from other constituents of the clarified stillage; and
c) purifying the separated betaine.

32. The process according to claim 31 wherein the step of clarifying further comprises initially centrifugally separating solids from liquid constituents prior to subjecting the stillage to microfiltration.

33. The process according to claim 31 wherein the clarified stillage from step (a) is enzymatically treated to hydrolize proteinaceous material.

34. The process according to claim 31 wherein the clarified stillage is concentrated to 50-75% solids and the resulting potassium sulfate crystals are removed.

35. The process according to claim 31 wherein the permeate from the microfiltration step is concentrated to as high a solids concentration as practicable before passing through said ion exclusion material.

36. The process according to claim 31 wherein said purifying step comprises the steps of ion exchange, evaporation to a concentration of 80-85% glycerol, further distillation and refining into glycerol having a purity of at least 99.7%.

37. The process according to claim 31 wherein said clarification, chromatographic separation, and purification are all a part of a continuous process.

* * * * *